United States Patent
El Hage et al.

(10) Patent No.: US 8,492,342 B2
(45) Date of Patent: Jul. 23, 2013

(54) PREPROCALCITONIN ANTIGEN T EPITOPES

(75) Inventors: Faten El Hage, Paris (FR); Vincent Stroobant, Ottignies (BE); Pierre G. Coulie, Kraainem (BE); Fathia Mami-Chouaib, Bourg la Reine (FR)

(73) Assignees: Institut Gustave Roussy, Villejuif (FR); Institut National de la Sante et de la Rescherche Medicale, Paris (FR)

( * ) Notice: Subject to any disclaimer, the term of this patent is extended or adjusted under 35 U.S.C. 154(b) by 523 days.

(21) Appl. No.: 12/664,956

(22) PCT Filed: Jun. 19, 2008

(86) PCT No.: PCT/IB2008/002625
§ 371 (c)(1),
(2), (4) Date: Mar. 11, 2010

(87) PCT Pub. No.: WO2009/010874
PCT Pub. Date: Jan. 22, 2009

(65) Prior Publication Data
US 2010/0184700 A1   Jul. 22, 2010

(30) Foreign Application Priority Data
Jun. 22, 2007 (EP) .................................... 07290777

(51) Int. Cl.
*A61K 38/00*   (2006.01)
*A61P 35/00*   (2006.01)

(52) U.S. Cl.
USPC ........................................................ 514/19.3

(58) Field of Classification Search
None
See application file for complete search history.

(56) References Cited

FOREIGN PATENT DOCUMENTS
WO   WO 01/75179   10/2001

OTHER PUBLICATIONS

Sidney et al., 2001, Hum. Immunol. vol. 62: 1200-1216.*
Moullec, et al., "The Complete Sequence of Human Preprocalcitonin", FEBS Lett., 167, pp. 93-97, 1984.
Minvielle, et al., "A Novel Calcitonin Carboxyl-terminal Peptide Produced in Medullary Thyroid . . . ", J. Biol. Chem., 266, pp. 24627-24631, 1991.
El Hage, et al., "Preprocalcitonin Signal Peptide Generates a Cytotoxic . . . ", Proceedings of the National Academy of Sciences of USA, 105, pp. 10119-10124, 2008.

* cited by examiner

*Primary Examiner* — Amy Juedes
(74) *Attorney, Agent, or Firm* — Morgan, Lewis, Bockius LLP

(57) ABSTRACT

The present invention is related to Preprocalcitonin antigen T epitopes, presented by the Major Histocompatibility Complex I (MHC I). These peptides can be used in cancer immunotherapy.

12 Claims, 7 Drawing Sheets

A

B

A

B

A

B

A

B

Figure 5:
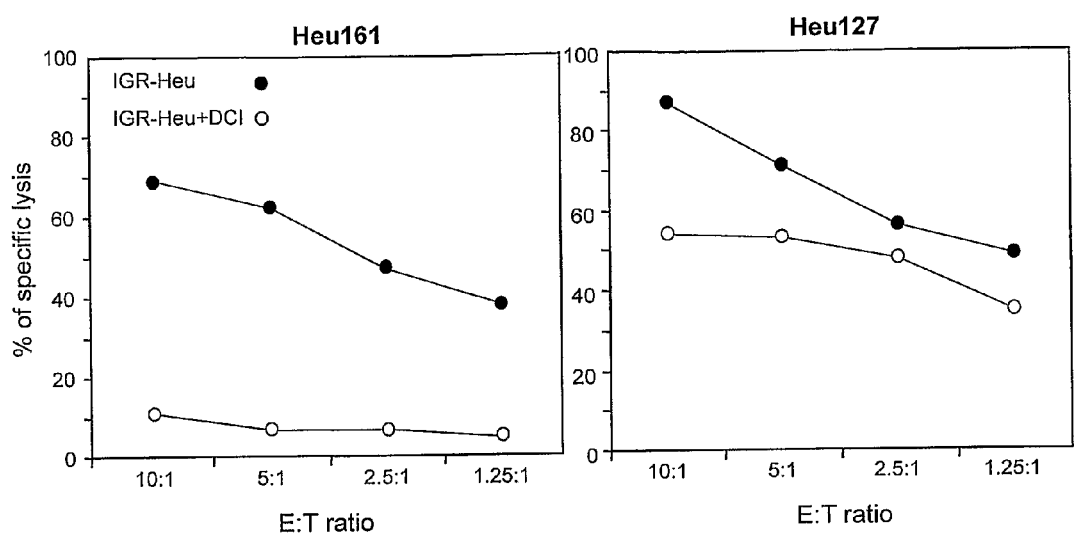
Figure 5:
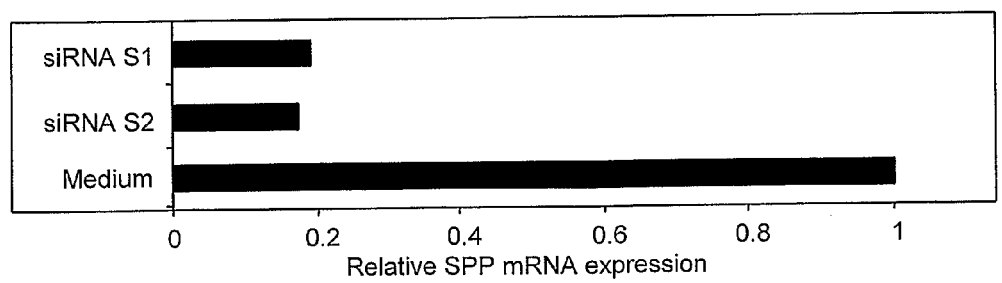

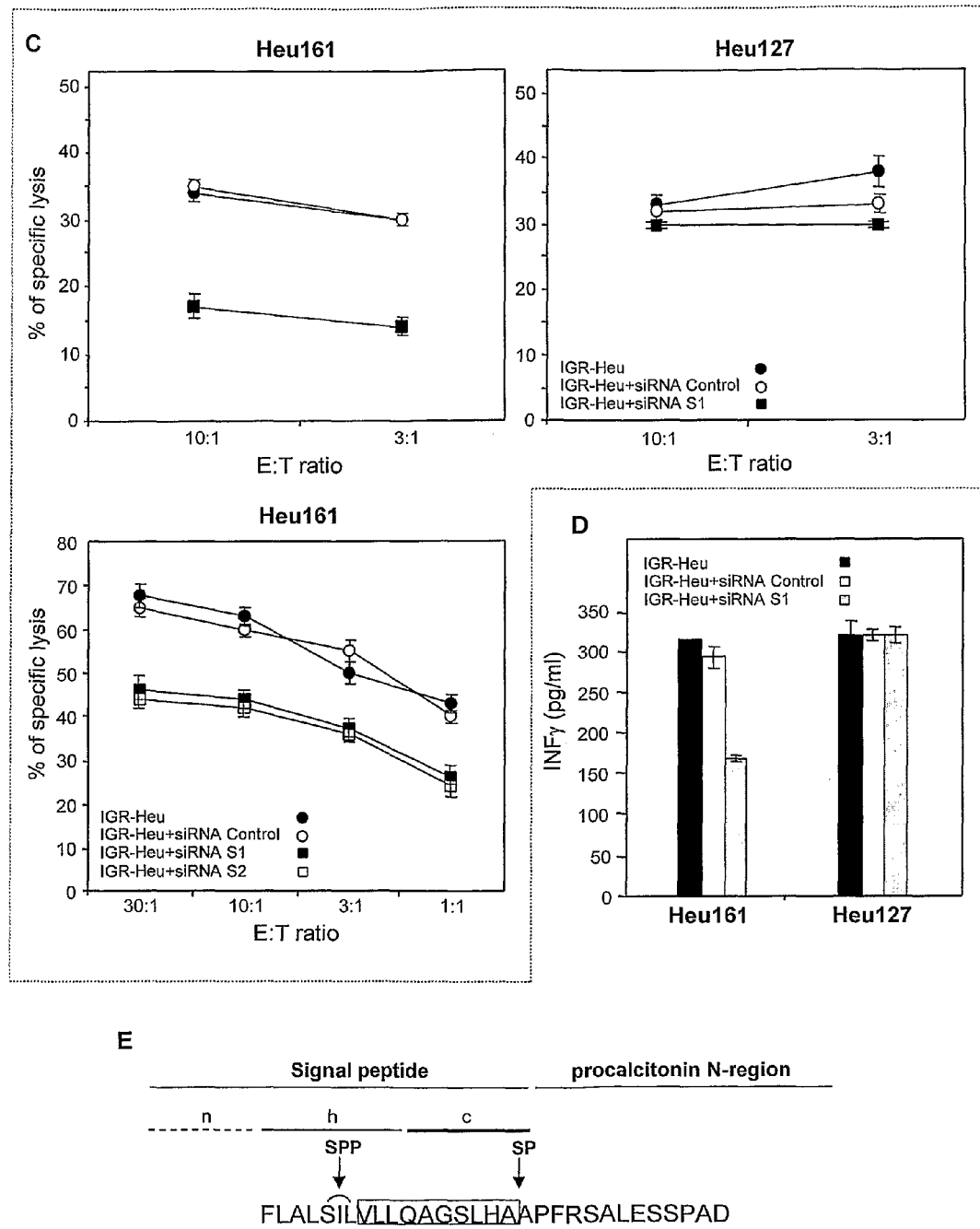
Figure 5 (followed)

SEQUENCE LISTING

```
<160> NUMBER OF SEQ ID NOS: 26

<210> SEQ ID NO 1
<211> LENGTH: 10
<212> TYPE: PRT
<213> ORGANISM: Homo sapiens

<400> SEQUENCE: 1

Val Leu Leu Gln Ala Gly Ser Leu His Ala
1               5                   10

<210> SEQ ID NO 2
<211> LENGTH: 11
<212> TYPE: PRT
<213> ORGANISM: Homo sapiens

<400> SEQUENCE: 2

Leu Val Leu Leu Gln Ala Gly Ser Leu His Ala
1               5                   10

<210> SEQ ID NO 3
<211> LENGTH: 21
<212> TYPE: DNA
<213> ORGANISM: Artificial
<220> FEATURE:
<223> OTHER INFORMATION: siRNA

<400> SEQUENCE: 3
gacaugccug aaacaaucat t                                                 21

<210> SEQ ID NO 4
<211> LENGTH: 21
<212> TYPE: DNA
<213> ORGANISM: Artificial
<220> FEATURE:
<223> OTHER INFORMATION: siRNA

<400> SEQUENCE: 4
ugauuguuuc aggcauguct g                                                 21

<210> SEQ ID NO 5
<211> LENGTH: 22
<212> TYPE: DNA
<213> ORGANISM: Artificial
<220> FEATURE:
<223> OTHER INFORMATION: PCR primer

<400> SEQUENCE: 5
ggtgtcatgg gcttccaaaa gt                                                22
```

```
<210> SEQ ID NO 6
<211> LENGTH: 22
<212> TYPE: DNA
<213> ORGANISM: Artificial
<220> FEATURE:
<223> OTHER INFORMATION: PCR primer

<400> SEQUENCE: 6
atcagcacat tcagaagcag ga                                              22

<210> SEQ ID NO 7
<211> LENGTH: 20
<212> TYPE: DNA
<213> ORGANISM: Artificial
<220> FEATURE:
<223> OTHER INFORMATION: PCR primer

<400> SEQUENCE: 7
atcttggtcc tgttgcaggc                                                 20

<210> SEQ ID NO 8
<211> LENGTH: 21
<212> TYPE: DNA
<213> ORGANISM: Artificial
<220> FEATURE:
<223> OTHER INFORMATION: PCR primer

<400> SEQUENCE: 8
tggagccctc tctctcttgc t                                               21

<210> SEQ ID NO 9
<211> LENGTH: 22
<212> TYPE: DNA
<213> ORGANISM: Artificial
<220> FEATURE:
<223> OTHER INFORMATION: PCR primer

<400> SEQUENCE: 9
cctcctgctg gctgcactgg tg                                              22

<210> SEQ ID NO 10
<211> LENGTH: 10
<212> TYPE: PRT
<213> ORGANISM: Artificial
<220> FEATURE:
<223> OTHER INFORMATION: Modidied peptide

<400> SEQUENCE: 10

Tyr Leu Leu Gln Ala Gly Ser Leu His Val
1               5                   10

<210> SEQ ID NO 11
<211> LENGTH: 10
<212> TYPE: PRT
<213> ORGANISM: Artificial
<220> FEATURE:
<223> OTHER INFORMATION: Modified peptide

<400> SEQUENCE: 11

Val Leu Leu Gln Ala Gly Ser Leu His Val
1               5                   10

<210> SEQ ID NO 12
<211> LENGTH: 10
<212> TYPE: PRT
<213> ORGANISM: Artificial
```

```
<220> FEATURE:
<223> OTHER INFORMATION: Modified peptide

<400> SEQUENCE: 12

Val Leu Leu Gln Ala Gly Ser Leu His Leu
1               5                   10

<210> SEQ ID NO 13
<211> LENGTH: 10
<212> TYPE: PRT
<213> ORGANISM: Artificial
<220> FEATURE:
<223> OTHER INFORMATION: Modified peptide

<400> SEQUENCE: 13

Leu Leu Leu Gln Ala Gly Ser Leu His Val
1               5                   10

<210> SEQ ID NO 14
<211> LENGTH: 47
<212> TYPE: PRT
<213> ORGANISM: Homo sapiens

<400> SEQUENCE: 14

Met Gly Phe Gln Lys Phe Ser Pro Phe Leu Ala Leu Ser Ile Leu Val
1               5                   10                  15

Leu Leu Gln Ala Gly Ser Leu His Ala Ala Pro Phe Arg Ser Ala Leu
            20                  25                  30

Glu Ser Ser Pro Ala Asp Pro Ala Thr Leu Ser Glu Asp Glu Ala
        35                  40                  45

<210> SEQ ID NO 15
<211> LENGTH: 41
<212> TYPE: PRT
<213> ORGANISM: Homo sapiens

<400> SEQUENCE: 15

Met Gly Phe Gln Lys Phe Ser Pro Phe Leu Ala Leu Ser Ile Leu Val
1               5                   10                  15

Leu Leu Gln Ala Gly Ser Leu His Ala Ala Pro Phe Arg Ser Ala Leu
            20                  25                  30

Glu Ser Ser Pro Ala Asp Pro Ala Thr
        35                  40

<210> SEQ ID NO 16
<211> LENGTH: 35
<212> TYPE: PRT
<213> ORGANISM: Homo sapiens

<400> SEQUENCE: 16

Met Gly Phe Gln Lys Phe Ser Pro Phe Leu Ala Leu Ser Ile Leu Val
1               5                   10                  15

Leu Leu Gln Ala Gly Ser Leu His Ala Ala Pro Phe Arg Ser Ala Leu
            20                  25                  30

Glu Ser Ser
        35

<210> SEQ ID NO 17
<211> LENGTH: 29
<212> TYPE: PRT
<213> ORGANISM: Homo sapiens

<400> SEQUENCE: 17
```

```
Met Gly Phe Gln Lys Phe Ser Pro Phe Leu Ala Leu Ser Ile Leu Val
1               5                   10                  15

Leu Leu Gln Ala Gly Ser Leu His Ala Ala Pro Phe Arg
            20                  25
```

<210> SEQ ID NO 18
<211> LENGTH: 41
<212> TYPE: PRT
<213> ORGANISM: Homo sapiens

<400> SEQUENCE: 18

```
Ser Pro Phe Leu Ala Leu Ser Ile Leu Val Leu Leu Gln Ala Gly Ser
1               5                   10                  15

Leu His Ala Ala Pro Phe Arg Ser Ala Leu Glu Ser Ser Pro Ala Asp
            20                  25                  30

Pro Ala Thr Leu Ser Glu Asp Glu Ala
            35                  40
```

<210> SEQ ID NO 19
<211> LENGTH: 39
<212> TYPE: PRT
<213> ORGANISM: Homo sapiens

<400> SEQUENCE: 19

```
Phe Leu Ala Leu Ser Ile Leu Val Leu Leu Gln Ala Gly Ser Leu His
1               5                   10                  15

Ala Ala Pro Phe Arg Ser Ala Leu Glu Ser Ser Pro Ala Asp Pro Ala
            20                  25                  30

Thr Leu Ser Glu Asp Glu Ala
            35
```

<210> SEQ ID NO 20
<211> LENGTH: 36
<212> TYPE: PRT
<213> ORGANISM: Homo sapiens

<400> SEQUENCE: 20

```
Leu Ser Ile Leu Val Leu Leu Gln Ala Gly Ser Leu His Ala Ala Pro
1               5                   10                  15

Phe Arg Ser Ala Leu Glu Ser Ser Pro Ala Asp Pro Ala Thr Leu Ser
            20                  25                  30

Glu Asp Glu Ala
            35
```

<210> SEQ ID NO 21
<211> LENGTH: 31
<212> TYPE: PRT
<213> ORGANISM: Homo sapiens

<400> SEQUENCE: 21

```
Leu Leu Gln Ala Gly Ser Leu His Ala Ala Pro Phe Arg Ser Ala Leu
1               5                   10                  15

Glu Ser Ser Pro Ala Asp Pro Ala Thr Leu Ser Glu Asp Glu Ala
            20                  25                  30
```

<210> SEQ ID NO 22
<211> LENGTH: 30
<212> TYPE: PRT
<213> ORGANISM: Homo sapiens

<400> SEQUENCE: 22

```
Phe Leu Ala Leu Ser Ile Leu Val Leu Leu Gln Ala Gly Ser Leu His
```

```
                1               5                   10                  15
Ala Ala Pro Phe Arg Ser Ala Leu Glu Ser Ser Pro Ala Asp
                20                  25                  30

<210> SEQ ID NO 23
<211> LENGTH: 29
<212> TYPE: PRT
<213> ORGANISM: Homo sapiens

<400> SEQUENCE: 23

Phe Leu Ala Leu Ser Ile Leu Val Leu Leu Gln Ala Gly Ser Leu His
1               5                   10                  15

Ala Ala Pro Phe Arg Ser Ala Leu Glu Ser Ser Pro Ala
                20                  25

<210> SEQ ID NO 24
<211> LENGTH: 9
<212> TYPE: PRT
<213> ORGANISM: Homo sapiens

<400> SEQUENCE: 24

Leu Leu Gln Ala Gly Ser Leu His Ala
1               5

<210> SEQ ID NO 25
<211> LENGTH: 11
<212> TYPE: PRT
<213> ORGANISM: Homo sapiens

<400> SEQUENCE: 25

Val Leu Leu Gln Ala Gly Ser Leu His Ala Ala
1               5                   10

<210> SEQ ID NO 26
<211> LENGTH: 9
<212> TYPE: PRT
<213> ORGANISM: Homo sapiens

<400> SEQUENCE: 26

Val Leu Leu Gln Ala Gly Ser Leu His
1               5
```

PREPROCALCITONIN ANTIGEN T EPITOPES

RELATED APPLICATIONS

The present application is a U.S. National Phase Application of International Application No. PCT/IB2008/002625 (filed Jun. 19, 2008), which claims priority to European Patent Application No. 07290777.7 (filed Jun. 22, 2007), all of which are hereby incorporated by reference in their entirety.

SEQUENCE LISTING SUBMISSION VIA EFS-WEB

A computer readable text file, entitled "045636-5124-SeqListing.txt," created on or about Dec. 15, 2009 with a file size of about 7 kb contains the sequence listing for this application and is hereby incorporated by reference in its entirety.

The present invention is related to preprocalcitonin T epitopes and their uses in cancer immunotherapy.

The analysis of tumor-reactive CTLs derived from patients with various solid tumors had led to promising new treatments for malignant diseases, either by expanding the T cells in vitro before transferring them with IL-2 into patients (GATTINONI et al., Nat Rev Immunol, 6, 383-93, 2006), or by identifying their target Ag which can then be used in therapeutic vaccines. A large number of tumor-associated Ags recognized by CTLs, derived either from PBL or tumor-infiltrating lymphocytes (TIL), have been identified. Most of this work was conducted with malignant melanoma tumors. Unfortunately, clinical studies indicate that despite an increase in the frequency of anti-tumor CD8 T cells, the efficacy of current therapeutic vaccines remains limited in metastatic melanoma patients (ROSENBERG et al., Nat Med, 10, 909-15, 2004). Current studies are focusing on a better understanding of the mechanisms of rare tumor regressions observed (GERMEAU et al., J Exp Med, 201, 241-8, 2005; LURQUIN et al., J Exp Med, 201, 249-57, 2005), the activation state of anti-vaccine CD8 T cells and their capacity to migrate to the tumor site and on determining the local mechanisms governing the pacific coexistence of tumor-specific T cells and tumor cells.

Much less is known about the antigenicity and susceptibility to CTL attack of human lung tumors. Most of these tumors are non-small cell lung carcinomas (NSCLC), a large group that includes squamous-cell (SCC), adeno- (ADC) and large-cell (LCC) carcinomas. NSCLC can be infiltrated by TCRα/β T cells (ECHCHAKIR et al., Int Immunol, 12, 537-46, 2000). The identified T cell target Ags include peptides encoded by the HER2/neu proto-oncogene (YOSHINO et al., Cancer Res, 54, 3387-90, 1994), which is overexpressed in many lung tumors, and by several genes that were found to contain a point mutation in tumor cells compared to autologous normal cells. These mutated genes include elongation factor 2 (HOGAN et al., Cancer Res, 58, 5144-50, 1998), malic enzyme (KARANIKAS et al., Cancer Res, 61, 3718-24, 2001), mutated α-actinin-4 (ECHCHAKIR et al., Cancer Res, 61, 4078-83, 2001) and NFYC (TAKENOYAMA et al., Int J Cancer, 118, 1992-7, 2006). In addition, several cancer/germline genes are expressed in NSCLC (WEYNANTS et al., Int J Cancer, 56, 826-9, 1994; SHICHIJO et al., Int J Cancer, 64, 158-65, 1995; YOSHIMATSU et al., J Surg Oncol, 67, 126-9, 1998; JANG et al., Cancer Res, 61, 7959-63, 2001; GRUNWALD et al., Int J Cancer, 118, 2522-8, 2006), which should lead to the presence of tumor-specific Ags at the surface of cancer cells. However, spontaneous T cell responses against MAGE-type Ags have thus far not been observed in lung cancer patients. Therefore, identification of new lung cancer Ags, in particular those shared by tumors of several patients, would help the design and immunological monitoring of novel vaccination strategies in lung cancer.

Most antigenic peptides recognized by CD8 T cells originate from degradation in proteasomes of intracellular mature proteins and their transport, by the transporter associated with antigen processing (TAP), from the cytosol into the ER (for review see ROCK & GOLDBERG, Annu Rev Immunol, 17, 739-79, 1999). The resulting peptides of 9 to 10 aa bind MHC class I (MHC-I) molecules and are then conveyed to the cell surface. An increasing number of epitopes recognized by tumor-reactive T cells have been reported to result from non-classical mechanisms acting at the transcription, splicing or translational levels (for review see MAYRAND & GREEN, Immunol Today, 19, 551-6, 1998). It is noteworthy that a number of tumor epitopes are poorly processed by DCs, which are unique in their capacity to process Ags and to prime CD8 T cells, but which constitutively express immunoproteasomes (MOREL et al., Immunity, 12, 107-17, 2000; CHAPATTE et al., Cancer Res, 66, 5461-8, 2006).

The inventors have identified a peptidic epitope recognized on a human non-small cell lung carcinoma by a cytotoxic T lymphocyte clone derived from autologous tumor-infiltrating lymphocytes. They found that this peptide, which is presented by HLA-A2, is derived from the carboxy-terminal region of the preprocalcitonin signal peptide, and is processed independently of proteasomes and the transporter associated with antigen processing.

Preprocalcitonin is encoded by the CALCA gene, which also codes for the α-calcitonin gene-related peptide (α-CGRP). The CALCA gene includes 5 introns and 6 exons and its primary RNA transcript exhibits tissue-specific alternative splicing (JONAS et al., Proc Natl Acad Sci USA, 82, 1994-8, 1985; ROSENFELD et al., Nature, 304, 129-35, 1983). Exons 1, 2, 3 and 4 are joined to produce the calcitonin mRNA in thyroid C-cells, while exons 1, 2, 3, 5 and 6 form the α-CGRP mRNA in neuronal cells (MORRIS et al., Nature, 308, 746-8, 1984). Mature α-CGRP is an endogenous vasodilatory peptide of 37 aa widely distributed in the body (ZAIDI et al., Crit Rev Clin Lab Sci, 28, 109-74, 1990). The calcitonin mRNA encodes a 141-amino acid precursor protein, preprocalcitonin, which includes a N-terminal signal sequence of 25 residues. The cleavage of the signal sequence results in procalcitonin, which contains 116 aa, comprising a N-terminal region (57 aa), calcitonin itself (32 aa), and a C-terminal peptide, katacalcin (21 aa) (ROSENFELD et al., Nature, 304, 129-35, 1983). The signal sequence of preprocalcitonin is also present in the α-CGRP preprohormone.

Calcitonin is a hormone primarily involved in protecting the skeleton during periods of "calcium stress" such as growth, pregnancy and lactation (STEVENSON et al., Lancet, 2, 769-70, 1979; AUSTIN & HEATH, N Engl J Med, 304, 269-78, 1981). Calcitonin is known to be produced at high levels by medullary thyroid carcinoma (MTC) and by some lung carcinomas (COOMBES et al., Lancet, 1, 1080-3, 1974; MILHAUD et al., Lancet, 1, 462-3, 1974). Elevated calcitonin plasma levels are diagnostic and prognostic markers in these tumors (COOMBES et al., Lancet, 1, 1080-3, 1974). The aberrant expression of gene CALCA in lung cancer cells is not well understood, but results in part from promoter demethylation (BAYLIN et al., Cancer Res, 46, 2917-22, 1986) and loss of transcriptional repression (SYMES et al., FEBS Lett, 306, 229-33, 1992).

It has been proposed to use dendritic cells (DCs) pulsed with the mature calcitonin polypeptide for the immunotherapy of MTC (SCHOTT et al., Cancer Immunol Immunother, 51, 663-8, 2002). However, it has not been suggested until now that other regions of the calcitonin precursor may play a part in the induction of an anti-tumoral immune response.

Consequently, a subject of the present invention is an isolated immunogenic peptide constituting a T epitope presented by MHC I, characterized in that it consists of a fragment of 8 to 11 consecutive amino acids of preprocalcitonin, and more specifically of the signal peptide thereof.

According to a preferred embodiment of the invention, said peptide comprises the sequence (one-letter code) VLLQAGSLHA (SEQ ID NO: 1). Preferably, said peptide is selected among a peptide having the sequence VLLQAGSLHA (SEQ ID NO: 1), and a peptide having the sequence LVLLQAGSLHA (SEQ ID NO: 2).

This peptide can optionally further be modified in order to increase its immunogenicity, for instance by substitution of one or more of the amino acids of the native sequence with one or more amino acids favourable to the affinity for HLA-A2 and/or to the stability of the peptide/HLA-A2 molecule complex.

Amino acids that are favourable to the affinity for a given MHC I molecule and/or to the stability of the peptide/HLA-A2 molecule complex may, for example, consist of anchor residues, and in particular the secondary anchor residues, known for HLA-A2 alleles. These anchor residues can be readily identified by consulting the available databases, such as the SYFPEITHI base (Rammensee et al., Immunogenetics, 50, 213-219, 1999), or the BIMAS base (Parker et al., J. immunol. 152, 163, 1994).

By way of example of substitutions making it possible to increase the immunogenicity of a peptide of the invention, mention will be made of:

the substitution of the N-terminal amino acid of said peptide with a tyrosine, as described in PCT application WO 02/08716, or (in the case of the peptide SEQ ID NO: 1), with a leucine;

the substitution of the C-terminal alanine of peptide SEQ ID NO: 1 with a valine or a leucine.

Particularly preferred modified peptides derived from SEQ ID NO: 1 are those selected from the group consisting of YLLQAGSLHV (SEQ ID NO: 10) VLLQAGSLHV (SEQ ID NO: 11), VLLQAGSLHL (SEQ ID NO: 12) and LLLQAGSLHV (SEQ ID NO: 13).

A subject of the present invention is also compositions comprising at least one immunogenic peptide in accordance with the invention.

They may be multiepitope compositions capable of generating a polyspecific CTL response, and which, with the same, also comprise one or more other immunogenic epitope(s).

These other immunogenic epitopes may be peptides presented by MHC, for instance immunogenic peptides isolated from calcitonin or α-CGRP or from one or more other antigens, by way of example HER2/neu.

The multiepitope compositions in accordance with the invention may comprise, so that they can be widely used on a population whose individuals carry different HLA alleles, epitopes presented by various MHC I molecules. They may also comprise, in addition, at least one epitope presented by an MHC II molecule and capable of inducing a T-helper response.

According to a preferred embodiment of a composition in accordance with the invention, it comprises at least one chimeric polypeptide comprising one or more copies of an immunogenic peptide in accordance with the invention fused to an heterologous polypeptide (i.e a polypeptide which is not a part of the signal peptide of calcitonin).

For instance, in the case of a multiepitope composition, said heterologous sequence also comprises one or more copies of at least one other immunogenic peptidic epitope. Also, an immunogenic peptide according to the invention can be inserted into *Bordetella pertussis* adenylate cyclase (CyA). Since the receptor of CyA is the CD11b receptor and because dendritic cells express CD11b receptor, such a construct allows the immunogenic peptide to be targeted directly to the dendritic cells. (DADAGLIO et al., Int. Immunol, 15, 1423-1430, 2003)

The chimeric polypeptide can be readily obtained by methods known per se, and in particular by conventional recombinant DNA techniques.

The present invention also encompasses polynucleotides encoding an immunogenic peptide or a chimeric polypeptide in accordance with the invention.

These polynucleotides can be inserted in an appropriate expression vector, under transcriptional control of a suitable promoter, in order to allow the expression of the immunogenic peptide or the chimeric polypeptide in an host cell or organism. The choice of the expression vector depends on the host cell or organism where the expression is desired. For instance, for production of a polypeptide in bacteria or in eukaryotic, vectors with respectively a bacterial promoter or a eukaryotic promoter will be used. If it is intended to administrate the polynucleotide to a patient to be treated, one will preferably naked DNA plasmids, or viral vectors that cause transient expression, such as adenovirus-, lentivirus-, or vaccinia virus-derived vectors.

Compositions of the invention may also comprise dendritic cells, pulsed with a peptide, or a multiepitope composition of the invention, or transformed with a polynucleotide of the invention, inserted in an appropriate expression vector.

A subject of the present invention is also the use of an immunogenic peptide epitope, of a composition or of a polynucleotide in accordance with the invention, for obtaining a medicinal product, and in particular a medicinal product intended for antitumor immunotherapy, and in particular for the treatment of tumors expressing calcitonin and/or α-CGRP. This encompasses in particular lung carcinomas, including small cell lung carcinomas as well as non-small cell lung carcinomas and medullary thyroid carcinoma.

The peptides of the invention can in particular be used for obtaining medicinal products intended for the treatment of HLA-A*0201 patients. The present invention also encompasses the medicinal products comprising, as active principle, at least one immunogenic peptide, one composition or one polynucleotide in accordance with the invention. According to a preferred embodiment of the present invention, said medicinal products are vaccines for antitumoral immunotherapy. Medicinal products in accordance with the invention can also comprise the usual excipients, and also adjuvants conventionally used in immunotherapy and which make it possible, for example, to promote the administration of the active principle, to stabilize it, to increase its immunogenicity, etc. Examples of suitable adjuvants include CpG oligodeoxynucleotides, Apoptosis-Inducing Factor (AIF), Heat Shock Protein (HSP), Toll-like Receptors (TLRs) to activate immature dendritic cells, and cytokines and chemokines such as IL-7, IL-12, IL-15 and Granulocyte Macrophage Colony Stimulating Factor (GM-CSF).

In order to further improve the antitumoral response triggered by the immunogenic peptides of the invention, they can further be used in combination with other antitumoral agents.

By way of non limitative examples they can be combined with:

chemokines such as MIP3α (CCL20) and/or RANTES (CCL5), can be injected at the site of the tumor to be treated, in order to promote CTL migration toward the tumor;

cytotoxic agents which make tumor cells more sensitive to apoptotic induction, and more particularly inhibitors of the signaling pathway initiated by EGF-R (epidermal growth factor receptor), for instance wild-type protein p53, chemokine SDF-1, 1-methytryptophan (an inhibitor of indoleamine 2-3 dioxygenase), tyrosine kinases inhibitors, such as erlotinib, or antibodies against EGF-R, such as cetuximab.

The present invention will be understood more thoroughly from the further description which follows, which refers to non-limiting examples illustrating the identification of a preprocalcitonin epitope recognized by CTLs in lung or MTC cells.

LEGENDS OF THE DRAWINGS

Figure 1:
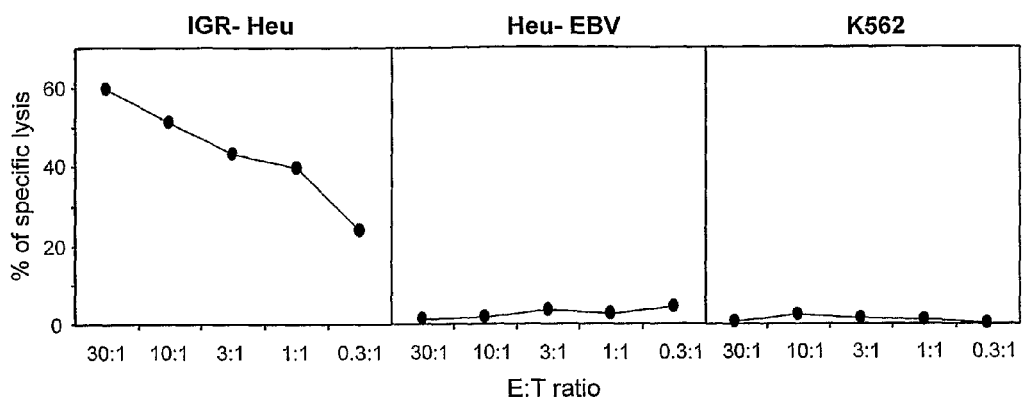
Figure 1:
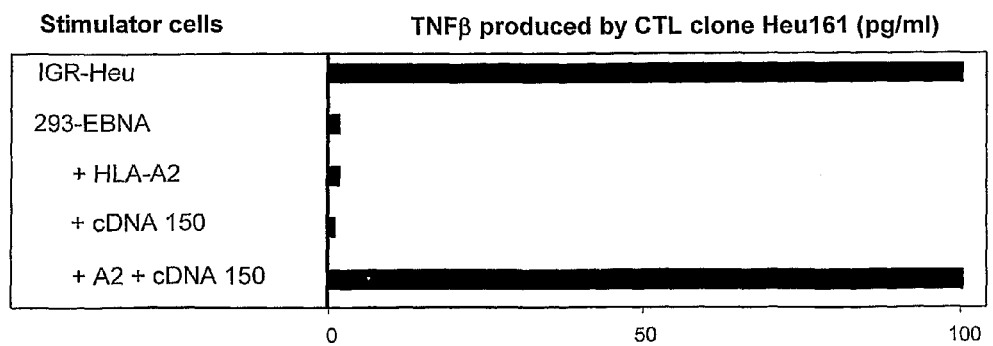

FIG. 1: A. Cytotoxic activity of CTL clone Heu161 towards tumor cells IGR-Heu, autologous EBV-transformed B cells (Heu-EBV) and K562. Cytolytic activity was measured in a conventional 4-h $^{51}$Cr-release assay performed in triplicate. E/T ratios are indicated. B. Identification of a cDNA clone encoding the Ag recognized by the CTL clone. Heu161 was stimulated by 293-EBNA cells cotransfected with vectors pCEP4 containing cDNA clone 150 and pcDNA3.1 containing an HLA-A*0201 sequence. Control stimulator cells included IGR-Heu, and 293-EBNA transfected with cDNA 150 or HLA-A2 alone. The concentration of TNFβ released in medium was measured using TNF-sensitive WEHI-164cl13 cells.

Figure 2:
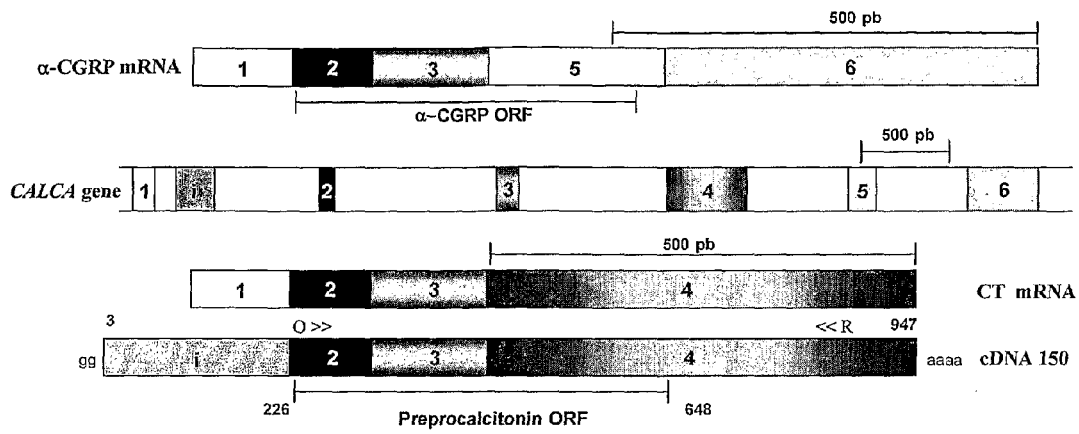

FIG. 2: A. Representation of cDNA 150 compared to the calcitonin and α-CGRP gene and transcripts. Numbered boxes represent exons. Arrows indicate forward (O) and reverse (R) primers used in RT-PCR analysis. B. Minigenes used to identify the region coding for the antigenic peptide. A series of truncated constructs were prepared and cotransfected into 293-EBNA cells with HLA-A2 cDNA. The corresponding encoded sequences are shown: peptide fragment 1-47 corresponds to SEQ ID NO: 14, peptide fragment 1-41 corresponds to SEQ ID NO: 15, peptide fragment 1-35 corresponds to SEQ ID NO: 16, peptide fragment 1-29 corresponds to SEQ ID NO: 17, peptide fragment 7-47 corresponds to SEQ ID NO: 18, peptide fragment 9-47 corresponds to SEQ ID NO: 19, peptide fragment 12-47 corresponds to SEQ ID NO: 20, peptide fragment 17-47 corresponds to SEQ ID NO: 21, peptide fragment corresponds 9-38 to SEQ ID NO: 22, peptide fragment 9-37 corresponds to SEQ ID NO: 23. Recognition by CTL clone Heu161 was assessed by TNFβ secretion assay.

Figure 3:
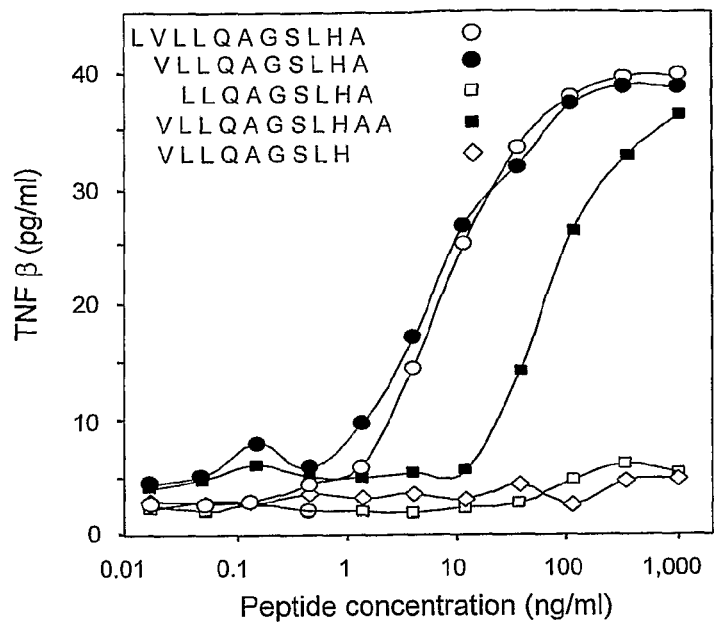
Figure 3:
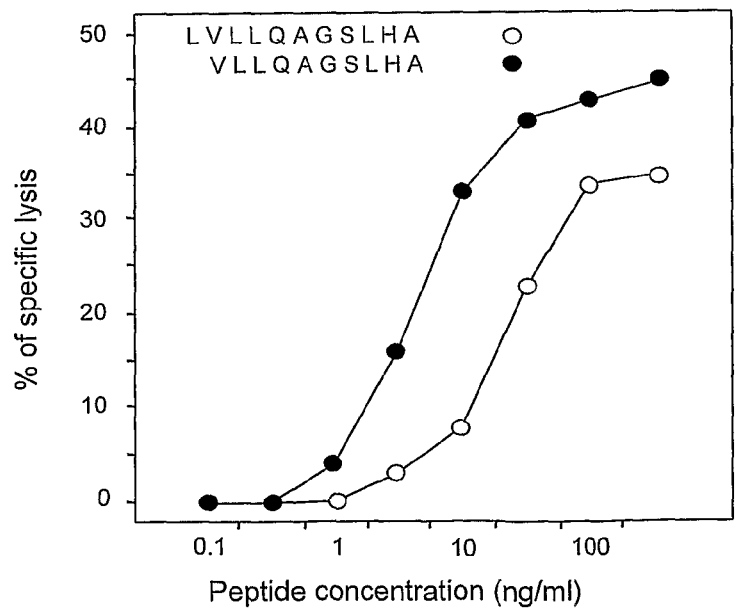

FIG. 3: Identification of the antigenic peptide recognized by CTL clone Heu161. A. CTL stimulation with purified synthetic peptides. Peptides were loaded on allogeneic HLA-A2$^+$ MZ2-MEL.3.1 melanoma cells for 60 min at room temperature before addition of CTL clone Heu161. TNF release was measured 16 h later. Empty circles represent the results obtained with peptide SEQ ID NO: 1, full circles represent the results obtained with peptide SEQ ID NO: 2, empty squares represent the results obtained with peptide SEQ ID NO: 24, full squares represent the results obtained with peptide SEQ ID NO: 25 and empty diamonds represent the results obtained with peptide SEQ ID NO: 26. B. Lytic activity of CTL clone on peptide-pulsed cells. $^{51}$Cr-labeled Heu-EBV-B cells were incubated over 60 min with the indicated concentrations of peptides before addition of CTL clone Heu161 at an E/T cell ratio of 10:1. Chromium release was measured after 4 h. Empty circles represent the results obtained with peptide SEQ ID NO: 1, full circles represent the results obtained with peptide SEQ ID NO: 2

Figure 4:
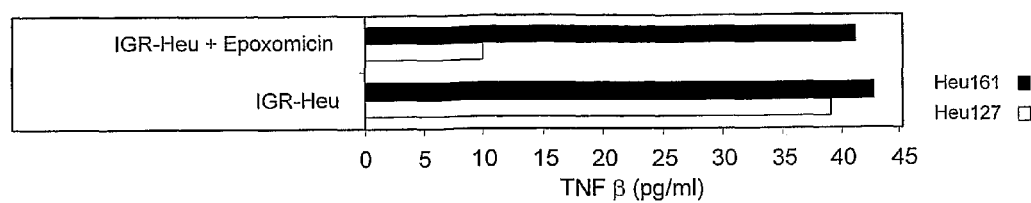
Figure 4:
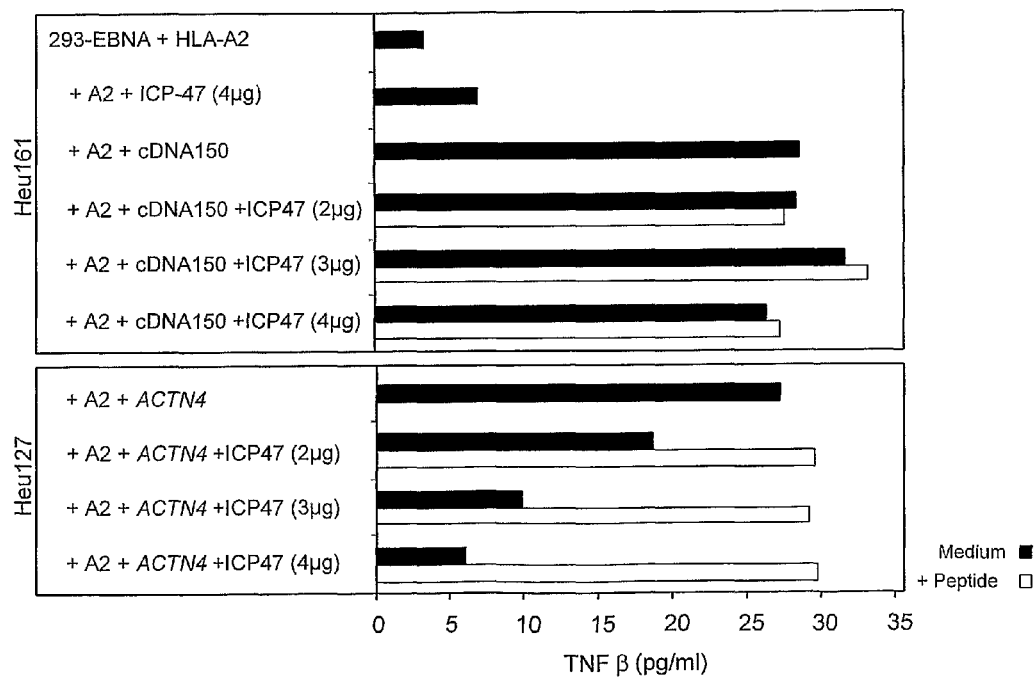

FIG. 4: Processing of the preprocalcitonin$_{16-25}$ peptide is proteasome- and TAP-independent. A. IGR-Heu target cells were incubated for 2 h at 37° C. in the presence or absence of the proteasome-specific inhibitor epoxomicin, and then Heu161 cells were added. The autologous Heu127 clone, recognizing on IGR-Heu a proteasome-dependent mutated α-actinin-4 peptide, was included as a positive control. TNFβ released in medium after 24 h of culture was measured as above. B. 293-EBNA cells were cotransfected with pCEP4 containing either cDNA 150 (upper panel) or the mutated α-actinin-4 cDNA (lower panel), with pcDNA3.1 containing an HLA-A*0201 construct, and with various amounts of vector pBJi-neo containing IPC47 cDNA. CTL clones Heu161 (upper panel) or Heu127 (lower panel) were then added. Controls included 293-EBNA cells transfected with HLA-A2 or pBJi-neo-IPC47 alone, and incubation of transfectants with either preprocalcitonin or α-actinin-4 peptides. Data shown are representative of four independent experiments.

FIG. 5: Processing of the preprocalcitonin$_{16-25}$ antigenic peptide involves SP and SPP. A. IGR-Heu tumor cells were incubated for 2 h at 37° C. with the serine protease inhibitor dichloroisocoumarin (DCI) at 250 μM, before addition of anti-preprocalcitonin (left panel) or anti-α-actinin-4 (right panel) CTL clones. B. Analysis of SPP mRNA expression by real-time RT-PCR analysis. Total RNA extracted from IGR-Heu tumor cells, electroporated or not with siRNA targeting SPP (siRNA-S1, siRNA-S2), was reverse-transcribed and quantified by TaqMan as described in Materials and Methods. C. Effect of SPP extinction on tumor cell recognition. Lytic activity of CTL clones Heu161 and Heu127 against IGR-Heu target cells, electroporated or not with siRNA-S1, siRNA-S2 or control siRNA, determined by a conventional 4 h $^{51}$Cr-release assay at the indicated E/T ratios. Two representative experiments of six are shown for CTL clone Heu161. D. Production of IFNγ by Heu161 and Heu127 CTL clones stimulated with tumor cells electroporated or not with siRNA-S1 or control siRNA. E. The preprocalcitonin$_{16-25}$ antigenic peptide is located at the C-terminus of the signal sequence of the calcitonin hormone precursor. The optimal peptide recognized by CTL clone Heu161 is boxed. Arrows indicate the signal peptidase (SP) and the approximate signal peptide peptidase (SPP) cleavage sites. The n, h and c regions in the preprocalcitonin signal peptide were predicted using SignalP 3.0 software.

Figure 6:
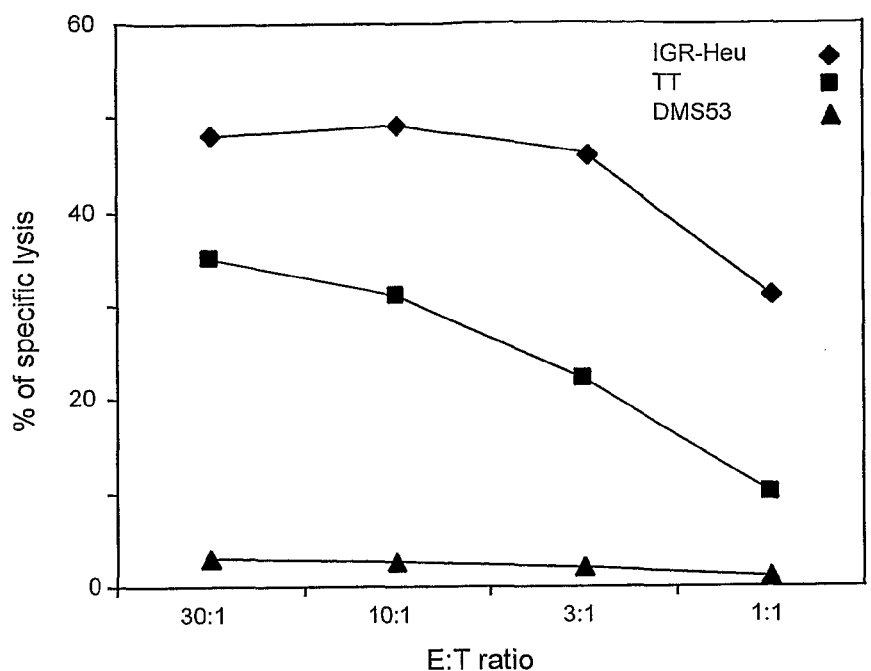
Figure 6:
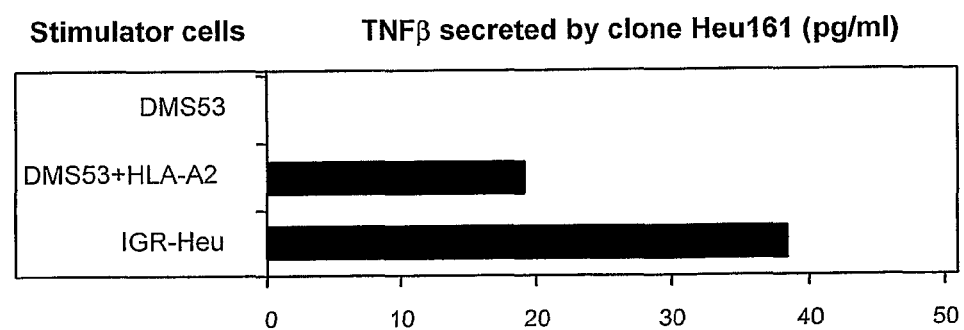
Figure 6:
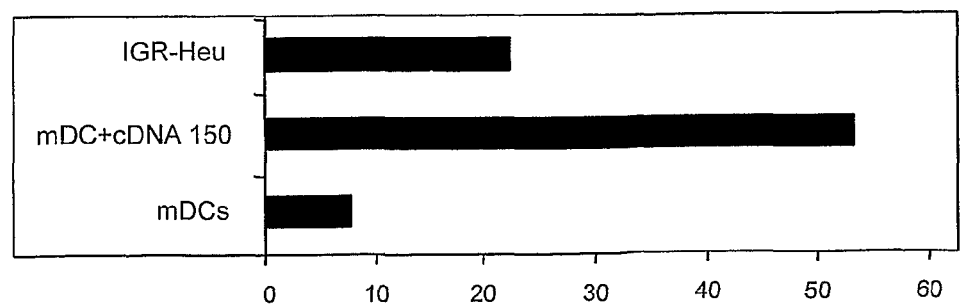

FIG. 6: A. Cytotoxic activity of CTL Heu161 against allogeneic MTC (TT) and SCLC (DMS53) cell lines. Autologous IGR-Heu tumor cells were included as positive control. B. Recognition of HLA-A2-transfected DMS53 cells by CTL clone Heu161. DMS53 cells were transfected with the pcDNA3.1 vector containing HLA-A*0201 before addition of CTL clone Heu161. c. Recognition of mature DCs expressing calcitonin. Monocytes were isolated from the blood of an HLA-A2 healthy donor using magnetic beads and cultured for 6 days in the presence of recombinant IL-4 (100 ng/ml) and GM-CSF (250 ng/ml). After maturation by adding TNFα (20 ng/ml) for another 3 days, the DCs were transfected with cDNA clone 150 in vector pCEP4, and the amount of TNFβ released by Heu161 was measured 24 h later.

EXAMPLE 1

Materials and Methods

Derivation of the NSCLC Tumor Cell Line and the Autologous CTL Clone

The IGR-Heu NSCLC cell line was derived from a LCC sample of patient Heu (HLA-A2, A68, B7, B35, C4, C7) and maintained in culture as previously reported (ECHCHAKIR et al., Cancer Res, 61, 4078-83, 2001). The Heu161 clone was derived from autologous TILs and amplified in 96-well V-shaped microtitre plates (Nunc, Roskilde, Denmark) as described (ECHCHAKIR et al., Int Immunol, 12, 537-46, 2000).

Cytotoxicity Assays and TNFβ Release

Cytotoxic activity was measured by a conventional 4-h $^{51}$Cr-release assay using triplicate cultures in round-bottomed 96-well plates. Percent specific cytotoxicity was calculated conventionally; SD were <5%. IGR-Heu, Heu-EBV, K562 (derived from a patient with chronic myelogenous leukemia), TT (HLA-A2.1$^{+}$ MTC; ECACC, Salisbury, UK) and DMS53 (HLA-A2$^{-}$ SCLC; ECACC) cell lines were used as targets in cytotoxicity assays.

TNFβ was detected by measuring the cytotoxicity of the culture medium on TNF-sensitive WEHI-164c13 cells with a MTT colorimetric assay (ESPEVIK & NISSEN-MEYER, J Immunol Methods, 95, 99-105, 1986).

Construction and Screening of the cDNA Library

The cDNA library from IGR-Heu tumor cells was constructed as previously reported (ECHCHAKIR et al., Cancer Res, 61, 4078-83, 2001). Briefly, poly(A)$^{+}$ RNA was extracted from IGR-Heu using the Fastrack kit (Invitrogen, Groningen, the Netherlands) and was converted to cDNA with the Superscript Choice System (Gibco BRL) using an oligo(dT) primer. cDNA was then ligated to the pCEP4 plasmid (Invitrogen) as described (ECHCHAKIR et al., Cancer Res, 61, 4078-83, 2001). Recombinant plasmids were electroporated into *Escherichia coli* DH5α and selected with ampicillin. The library was divided into pools of approximately 100 cDNA clones. Each pool was amplified and plasmid DNA was extracted using the QIAprep8 plasmid kit (QIAGEN GmbH, Hilden, Germany). 293-EBNA cells (Invitrogen) were cotransfected with plasmid DNA of each pool of the cDNA library and expression vector pcDNA1/Amp (Invitrogen) containing an HLA-A*0201 cDNA clone using the LipofectAMINE reagent (Life Technologies). After 24 h, CTL clone Heu161 (3,000 cells/well) was added. After another 24 h, half of the medium was collected and its TNFβ content measured with the WEHI-164c13 cells using a MTT colorimetric assay.

Sequence Analysis and Localization of the Encoding Exon cDNA clone 150 was sequenced using the dideoxy chain method in an ABI 310 automated DNA sequencer (Perkin Elmer Applied Biosystems, Warrington, Great Britain). Computer search for sequence homology was performed using programs available at www.ncbi.nlm.nih.gov/blast/blast.cgi. Sequence alignments were performed with Geneworks® software (Intelligenetics, Mountain View, Calif.). To identify the antigenic peptide-encoding region, a panel of cDNA fragments were amplified from cDNA clone 150 by PCR using a series of primer pairs. PCR conditions were 3 min at 94° C., followed by 30 cycles consisting of 1 min at 94° C., 2 min at 60° C. and 3 min at 72° C., and a final elongation step of 10 min at 72° C. These PCR products were cloned into expression plasmid pcDNA3.1 using the Eukaryotic TOPO TA cloning kit (Invitrogen). The constructs were then subcloned into the pCEP4 expression vector to allow overexpression and cotransfected into 293-EBNA cells with the HLA-A2 cDNA clone.

For proteasomes and SP inhibition, 10$^{6}$ tumor cells were resuspended in 300 μl of media in the presence or absence of specific inhibitors. Briefly, cells were incubated for 2 h at 37° C. either with epoxomicin or DCI (Sigma, Saint Louis, Mich.), washed in phosphate-buffered saline and resuspended in 175 μl of "acid buffer" (a 1:1 mixture of 0.263 M citric acid and 0.132 M NaH2PO4 at pH 2.5) for 50 s. The cells were then neutralized by the addition of RPMI 1640, centrifuged and incubated for an additional 3 h at 37° C. in the presence or absence of inhibitors. None of the inhibitors was toxic at the given concentrations, as verified by trypan blue staining.

For SPP inhibition, we first tried the cysteine protease inhibitor Z-LL$_2$ ketone (Calbiochem, Darmstadt, Germany), which was reported to specifically block SPP activity (WEIHOFEN et al., J Biol Chem, 275, 30951-6, 2000). No conclusive results were obtained in functional assays. We thus used siRNA targeting human SPP, siRNA-S1 (5-GACAUGCCUGAAACAAUCAtt-3; SEQ ID NO: 3) and siRNA-S2 (5-UGAUUGUUUCAGGCAUGUCtg-3; SEQ ID NO: 4), purchased from Ambion (Austin, Tex. USA). Non-targeting siRNA (Ambion) were used as negative control (siRNA Control). Briefly, IGR-Heu cells were transfected by electroporation with 50 nM siRNA in a Gene Pulser Xcell Electroporation System (Bio-Rad; 300 V, 500 F) as previously described (LE FLOC'H et al., J Exp Med, 2007) and then allowed to grow for 72 h.

RT-PCR Analyses

Total RNA extraction and RT were performed as described (LAZAR et al., J Clin Endocrinol Metab, 84, 3228-34, 1999). PCR amplification was performed with DNA polymerase TaKaRa Taq (Takara Biomedicals, Shiga, Japan) using the forward primer O (5'-ggt gtc atg ggc ttc caa aag t; SEQ ID NO: 5) located at the 5' end of the open reading frame (ORF) and the reverse primer R (5'-atc agc aca ttc aga agc agg a; SEQ ID NO: 6) located at the 3' end of the ORF (FIG. 2A). PCR conditions were 5 min at 94° C., followed by 30 cycles consisting of 1 min at 94° C., 2 min at 63° C. and 2 min at 72° C., and a final elongation step of 10 min at 72° C. We verified that in these conditions, we were in a linear range of DNA amplification. The quantities of the amplified DNA were visualized with agarose gel stained with ethidium bromide.

Quantitative PCR analysis (Taq-man) was performed using the forward primer 5'-atc ttg gtc ctg ttg cag gc (SEQ ID NO: 7) located at the 5' end of exon 2, and the reverse primer 5'-tgg agc cct ctc tct ctt gct (SEQ ID NO: 8) located at the 3' end of exon 3 of the CALCA gene. The Taq-man probe primer was Fam 5'-cct cct gct ggc tgc act ggt g (SEQ ID NO: 9)-3' Tamra. Primers and probes were designed using Primer Express (Applied Biosystems, Foster City, Calif.) and Oligo 4 (National Biosciences, Plymouth, Minn.) software. The amount of RNA sample was normalized by the amplification of an endogenous control (18S). Relative quantification of transcripts was derived using the standard curve method (Applied Biosystems User Bulletin 2, ABI PRISM 7700 Sequence Detection system). 18S RNA primers and probes were used according to the manufacturer's instructions. PCR amplifications were performed using the Taq-man Universal Master Mix in standard conditions according to the manufacturer's instructions (LAZAR et al., J Clin Endocrinol Metab, 84, 3228-34, 1999).

For SPP mRNA expression, total RNA from IGR-Heu cells, transfected or not with siRNA-S 1 and siRNA-S2 targeting SPP, was extracted, reverse-transcribed and quantified by real-time RT-PCR analysis (TaqMan). PCR primers and probe were designed by Applied Biosystems and used according to the manufacturer's recommendations. The amount of RNA sample was normalized by amplification of an endogenous control (18S).

EXAMPLE 2

A CTL Clone Recognizing Autologous Lung Carcinoma Cells

Patient Heu (HLA-A2$^+$) is a now-disease-free lung cancer patient 11 years after resection of the primary tumor. LCC cell line IGR-Heu was derived from a tumor resected from the patient in 1996. Mononuclear cells infiltrating the primary tumor were isolated and stimulated with irradiated IGR-Heu tumor cells, irradiated autologous EBV-transformed B cells, and IL-2. Responder lymphocytes were cloned by limiting dilution and stimulated with the same mixture of tumor and EBV-B cells. Several tumor-specific CTL clones were obtained and classified into three groups on the basis of their TCRVβ sequence (ECHCHAKIR et al., Int Immunol, 12, 537-46, 2000). We previously reported that the first two groups of clones (represented by Heu127 and Heu171) recognized an antigenic peptide encoded by a mutated sequence in the α-actinin-4 (ACTN4) gene (ECHCHAKIR et al., Cancer Res, 61, 4078-83, 2001; ECHCHAKIR et al., Proc Natl Acad Sci USA, 99, 9358-63, 2002). Here we analyze the third group of clones, including clone Heu161, which expresses a Vβ3-Jβ1.2 TCR rearrangement. CTL clone Heu161 lysed the autologous tumor cell line, but not autologous EBV-B cells nor the NK-target K562 (FIG. 1A). The recognition of IGR-Heu by the CTL clone was inhibited by anti-HLA-A2 mAb MA2.1 (data not shown).

EXAMPLE 3

Identification of the Gene Encoding the Antigen Recognized by the HEU161 Clone A cDNA library prepared with poly(A)$^+$ RNA from IGR-Heu cells was cloned into expression plasmid pCEP4 (ECHCHAKIR et al., Cancer Res, 61, 4078-83, 2001). The library was divided into 264 pools of approximately 100 recombinant clones, and DNA was prepared from each pool. 293-EBNA cells were cotransfected with DNA from each pool and with an HLA-A*0201 construct. CTL clone Heu161 was added to the transfectants after 24 h; after another 24 h, supernatants were collected and their TNFβ content measured with TNF-sensitive WEHI-164c13 cells (ESPEVIK & NISSEN-MEYER, J Immunol Methods, 95, 99-105, 1986). A large proportion (85/264) of cDNA pools proved positive, suggesting that a surprisingly high frequency of approximately 0.4% of cDNA clones encoded the Ag. One pool of cDNA was subcloned and a cDNA clone, named 150, was isolated (FIG. 1B).

cDNA 150 was 956 by long and contained a polyadenylation signal and a poly(A) tail. Its sequence corresponded to that of gene CALCA, which codes for both the calcium-lowering hormone calcitonin and the calcitonin gene-related peptide α (α-CGRP). A primary transcript is spliced into either calcitonin or α-CGRP mRNA through tissue-specific alternative RNA processing (AMARA et al., Nature, 298, 240-4, 1982). cDNA 150 contains the complete calcitonin coding sequence, spanning exons 2, 3 and 4 of gene CALCA (FIG. 2A). However, its 5' end differs from that of the calcitonin cDNA sequences present in databanks by the presence of an intronic sequence of 213 nucleotides (data not shown).

EXAMPLE 4

Identification of the Antigenic Peptide

The region coding for the antigenic peptide was identified with truncated cDNA fragments cloned into expression plasmids (see Materials and Methods) and cotransfected with the HLA-A2 construct into 293-EBNA cells. As shown in FIG. 2B, a fragment encoding the first 41 residues of preprocalcitonin transferred the expression of the Ag, whereas a fragment encoding the first 35 residues did not. This result suggested that the antigenic peptide was included in a region spanning residues 27 to 41 of the protein. However, this region did not contain any discernible HLA-A2-binding motif, and none of a set of synthetic peptides covering this region was recognized by the CTL clone (data not shown).

We then prepared a series of calcitonin cDNA fragments truncated at their 5' end and engineered to contain an initiation codon and a Kozak consensus sequence. Screening with the CTL clone indicated that the antigenic peptide was contained within residues 9-47 (FIG. 2B). Further trimming narrowed down the peptide-encoding region to residues 9-38 (FIG. 2B). Among a set of overlapping peptides covering this region, only two were recognized by CTL clone Heu161: VLLQAGSLHA (SEQ ID NO: 1) and LVLLQAGSLHA (SEQ ID NO: 2), which are identical, but with an additional leucine in the latter peptide. As shown in FIG. 3A, both peptides sensitized HLA-A2$^+$ melanoma cells to recognition by CTL Heu161, with half-maximal effects obtained with about 10 nM of peptide. In a lysis assay, the decamer was slightly more efficient than the 11-mer peptide by a factor of about three (FIG. 3B). We concluded that the optimal antigenic peptide recognized by CTL clone Heu161 was VLLQAGSLHA (SEQ ID NO: 1) or preprocalcitonin$_{16-25}$. This peptide corresponds exactly to the C-terminal part of the preprocalcitonin signal peptide (LE MOULLEC et al., FEBS Lett, 167, 93-7, 1984).

EXAMPLE 5

Processing of the Antigenic Peptide

This localization of the peptide in the protein suggested that it could be processed in the ER independently of cytoplasmic proteasomes and TAP transporters. To examine the involvement of proteasomes, IGR-Heu tumor cells were treated with specific proteasome inhibitor epoxomicin (FIG. 4A). Using 10 μM, we observed no effect on recognition by anti-preprocalcitonin CTL clone Heu161 (FIG. 4A). In contrast, epoxomycin strongly inhibited stimulation of another autologous CTL clone, Heu127, which recognizes a mutated α-actinin-4 peptide (ECHCHAKIR et al., Cancer Res, 61, 4078-83, 2001). This was expected, since α-actinin-4 is a cytosolic protein that is degraded, at least in part, in proteasomes (GOLDBERG & ROCK, Nature, 357, 375-9, 1992). These results suggest that processing of the preprocalcitonin$_{16-25}$ peptide does not require proteasomal activity.

The involvement of TAP was tested by cotransfecting into 293-EBNA cells constructs coding for the antigenic peptide, for HLA-A2, and for the immediate-early protein ICP47 of herpes simplex virus type 1, which binds to and inhibits human TAP (BANKS et al., Virology, 200, 236-45, 1994). As shown in FIG. 4B, cotransfecting ICP47 had no detectable effect on recognition of the transfectants by anti-preprocalcitonin CTLs, whereas it strongly inhibited that by the anti-α-actinin-4 CTL clone. These results strongly suggest that processing of the preprocalcitonin$_{16-25}$ epitope is TAP-independent.

As the C-terminus of antigenic peptide VLLQAGSLHA (SEQ ID NO: 1) corresponded to the C-terminus of the preprocalcitonin signal sequence (LE MOULLEC et al., FEBS Lett, 167, 93-7, 1984), it was expected to be generated by type I signal peptidase (SP), which cuts off signal peptides from secretory proteins on the luminal side of the ER membrane (DALBEY et al., Protein Sci, 6, 1129-38, 1997). SP involvement was tested using the serine protease inhibitor dichloroisocoumarin (DCI), which prevents release of signal sequences from precursor proteins (RUSBRIDGE & BEYNON, FEBS Lett, 268, 133-6, 1990). Remarkably, pre-incubation of IGR-Heu tumor cells with DCI rendered them totally resistant to lysis by the anti-preprocalcitonin CTL clone (FIG. 5A). The same treatment had only a moderate effect on recognition by the anti-α-actinin-4 CTL clone (FIG. 5A), and this probably resulted from decreased expression of MHC-I molecules on the surface of DCI-treated tumor cells (data not shown). These results are compatible with involvement of SP in processing the preprocalcitonin$_{16-25}$ peptide.

After cleavage by SP, some of the signal sequences inserted in the ER membrane in a type II, or loop-like, orientation can be further cleaved by the intramembrane aspartic protease signal peptide peptidase (SPP) (reviewed in (MARTOGLIO & DOBBERSTEIN, Trends Cell Biol, 8, 410-5, 1998)). We therefore tried to specifically knock down SPP expression in IGR-Heu tumor cells with short interference (si)RNAs (see Materials and Methods). siRNA-S1 and siRNA-S2 specifically inhibit SPP expression in IGR-Heu at both RNA (FIG. 5B) and protein (data not shown) levels. Downregulation of SPP resulted in a strong decrease in the sensitivity of the tumor cells to lysis by the anti-preprocalcitonin, but not by the anti-α-actinin-4 CTL clone (FIG. 5C). Similar inhibition was observed when tumor cells were used to stimulate production of IFNγ by CTLs (FIG. 5D). Together, these results indicated that the preprocalcitonin$_{16-25}$ peptide was most likely processed by SP and SPP within the ER before being loaded on HLA-A2 molecules (FIG. 5E).

EXAMPLE 6

Expression of the Calcitonin Gene Product in Tumor Samples

Expression of the calcitonin transcript was tested in a panel of lung carcinoma samples and cell lines by RT-PCR analysis as described in Materials and Methods. Positive samples were selected by agarose gel stained with ethidium bromide. Twenty-seven out of 209 tumor samples and 5 out of 38 cell lines were positive (Table I).

TABLE I

Expression of the calcitonin transcript in lung tumors

|  | Tumor samples | Tumor cell lines |
|---|---|---|
| Non-small cell lung carcinomas |  |  |
| Squamous cell carcinomas | 7/122 | 0/3 |
| Adenocarcinomas | 10/61 | 0/7 |
| Large cell carcinomas | 2/8 | 1/5 |
| Undifferentiated carcinomas | 1/3 |  |
| Small cell lung carcinomas | 3/5 | 4/23 |

TABLE I-continued

Expression of the calcitonin transcript in lung tumors

|  | Tumor samples | Tumor cell lines |
|---|---|---|
| Neuroendocrine tumors | 3/6 | — |
| Bronchioalveolar tumors | 1/4 | — |

Quantitative gene expression analysis of the calcitonin transcript was then carried out on some of the positive samples, and results were normalized to 18S RNA (Table II). Levels of calcitonin gene expression in the 3 cell lines tested, namely LCC IGR-Heu, SCLC DMS53, and medullary thyroid carcinoma (MTC) TT, were at least 100-fold higher than those found in normal human thyroid. It is noteworthy that the level of expression observed in the two lung carcinoma cell lines was similar to that observed in the MTC cell line (Table II). High levels of expression of the calcitonin transcript were also detected in the tumor biopsy of patient Heu (Heu-T) and in several other lung carcinoma samples such as ADC 8 and ADC 14 (Table II).

TABLE II

Relative expression of calcitonin transcript in tumor cell lines and biopsies.

|  | Histological type | Relative expression of calcitonin transcript |
|---|---|---|
| Tumor cell lines |  |  |
| IGR-Heu | LCC | 191.34 |
| DMS53 | SCLC | 116.97 |
| TT | MTC | 259.57 |
| Tumor biopsies |  |  |
| NSCLC |  |  |
| 1 (Heu-T) | LCC | 14.93 |
| 2 | LCC | 0.02 |
| 3 | SCC | 0.28 |
| 4 | SCC | 0.82 |
| 5 | SCC | 0.11 |
| 6 | SCC | 0.17 |
| 7 | SCC | 0.02 |
| 8 | ADC | 19.43 |
| 9 | ADC | 4.86 |
| 10 | ADC | 0.02 |
| 11 | ADC | 0.00 |
| 12 | ADC | 12.82 |
| 13 | ADC | 9.92 |
| 14 | ADC | 29.65 |
| 15 | ADC | 1.00 |
| 16 | ADC | 7.26 |
| 17 | Undifferentiated | 7.57 |
| 18 | Undifferentiated | 13.64 |
| SCLC |  |  |
| 19 | SCLC | 0.14 |
| 20 | Neuroendocrine | 2.27 |
| 22 | Neuroendocrine | 0.74 |
| 23 | Bronchioalveolar | 0.02 |
| Normal tissues |  |  |
| Pool of human lung | Lung | 0.00 |
| Pool of human thyroid | Thyroid | 1.15 |

Next, we wished to verify that CTL clone Heu161 could also recognize other HLA-A2$^+$ cells that overexpressed the calcitonin gene product. As shown in FIG. 6A, CTL Heu161 efficiently lysed HLA-A2$^+$ MTC cell line TT. The weaker levels of lysis of TT compared to IGR-Heu cannot be explained by differences in CALCA gene expression levels (Table II), but rather by differences in adhesion/co-stimulatory molecule surface expression (LE FLOC'H et al., J Exp Med, 2007). As expected, CTL Heu161 did not lyse HLA-A2⁻ SCLC DMS53 cells, but did recognize these cells after transfection with an HLA-A2 construct (FIG. 6B). Finally, mature DCs derived from blood monocytes of a healthy HLA-A2⁺ donor and transfected with the calcitonin cDNA clone strongly activated CTL clone Heu161 (FIG. 6C). We conclude from these results that processing of the antigenic peptide preprocalcitonin$_{16-25}$ occurs in all cells tested, namely NSCLC as well as SCLC cells, MTC cells, melanoma cells, 293 embryonic kidney cells and DCs. Therefore it would appears that all cells expressing the calcitonin transcript at high levels can be recognized by the CTL clone described here.

Here we confirmed, using quantitative RT-PCR analysis, that gene CALCA was expressed at high levels in several NSCLC and SCLC cell lines and in lung tumor biopsies. It is noteworthy that calcitonin and α-CGRP preprohormones share their 75 N-terminal residues encoded by CALCA exons 2 and 3, and that the peptide preprocalcitonin$_{16-25}$ is also the prepro-α-CGRP$_{16-25}$ peptide. It is therefore likely that cells expressing the α-CGRP but not the calcitonin transcripts can also be recognized by CTLs such as Heu161. For this reason, we used PCR primers in exons 2 and 3, detecting both types of CALCA transcripts. We observed that IGR-Heu cells also expressed high levels of classical α-CGRP mRNA, as well as an alternatively spliced mRNA corresponding to exons 1-3, part of exon 4 and exons 5-6, as described in MTC cells (MINVIELLE et al., J Biol Chem, 266, 24627-31, 1991).

The invention claimed is:

1. A method of immunotherapy for treating a tumour in a subject comprising selecting a subject that expresses HLA-A*0201 and administering to the subject a T epitope peptide presented by MHC I selected from the group consisting of:
   a) the peptide of sequence: VLLQAGSLHA (SEQ ID NO: 1),
   b) the peptide of sequence: LVLLQAGSLHA (SEQ ID NO: 2),
   c) the peptide of SEQ ID NO: 1 having at least one of the following substitutions:
      the substitution of the N-terminal valine of SEQ ID NO: 1 with a tyrosine, or a leucine; and
      the substitution of the C-terminal alanine of SEQ ID NO: 1 with a valine or a leucine, and
   d) the peptide of SEQ ID NO: 2 having at least one of the following substitutions;
      the substitution of the N-terminal leucine of SEQ ID NO: 2 with a tyrosine; and
      the substitution of the C-terminal alanine of SEQ ID NO: 2 with a valine or a leucine.

2. The method according to claim 1, wherein the tumour expresses preprocalcitonin and/or α-CGRP.

3. The method of claim 1, wherein the peptide has the sequence VLLQAGSLHA (SEQ ID NO: 1).

4. The method of claim 1, wherein the peptide has a substitution of the N-terminal amino acid of SEQ ID NO: 1 with a tyrosine.

5. The method of claim 1, wherein the peptide has a substitution of the N-terminal amino acid of SEQ ID NO: 1 with a leucine.

6. The method of claim 1, wherein the peptide has a substitution of the C-terminal amino acid of SEQ ID NO: 1 with a valine.

7. The method of claim 1, wherein the peptide has a substitution of the C-terminal amino acid of SEQ ID NO: 1 with a leucine.

8. The method of claim 1, wherein the peptide has the sequence LVLLQAGSLHA (SEQ ID NO: 2).

9. The method of claim 1, wherein the peptide has a substitution of the N-terminal amino acid of SEQ ID NO: 2 with a tyrosine.

10. The method of claim 1, wherein the peptide has a substitution of the C-terminal amino acid of SEQ ID NO: 2 with a valine.

11. The method of claim 1, wherein the peptide has a substitution of the C-terminal amino acid of SEQ ID NO: 2 with a leucine.

12. The method of claim 1, wherein the peptide has a substitution of the N-terminal amino acid of SEQ ID NO: 1 with a leucine and a substitution of the C-terminal amino acid of SEQ ID NO: 1 with a valine.

* * * * *